United States Patent
Kulkarni et al.

(10) Patent No.: US 11,390,594 B2
(45) Date of Patent: Jul. 19, 2022

(54) PROCEDURE FOR THE PREPARATION OF 2-CYANOIMINO-1,3-THIAZOLIDINE

(71) Applicant: Bayer CropScience LP, St. Louis, MO (US)

(72) Inventors: Shekhar Kulkarni, Overland Park, KS (US); Eric Rivadeneira, Overland Park, KS (US)

(73) Assignee: BAYER CROPSCIENCE LP, St. Louis, MO (US)

( * ) Notice: Subject to any disclaimer, the term of this patent is extended or adjusted under 35 U.S.C. 154(b) by 149 days.

(21) Appl. No.: 16/929,804

(22) Filed: Jul. 15, 2020

(65) Prior Publication Data

US 2020/0347024 A1    Nov. 5, 2020

Related U.S. Application Data

(62) Division of application No. 15/759,574, filed as application No. PCT/US2016/051287 on Sep. 12, 2016, now Pat. No. 10,752,600.

(60) Provisional application No. 62/218,736, filed on Sep. 15, 2015.

(51) Int. Cl.
  *C07D 277/18*    (2006.01)
  *C07D 417/06*    (2006.01)
  *A01N 43/78*    (2006.01)

(52) U.S. Cl.
  CPC ........... *C07D 277/18* (2013.01); *A01N 43/78* (2013.01); *C07D 417/06* (2013.01)

(58) Field of Classification Search
  CPC ........................... C07D 417/06; C07D 277/18
  See application file for complete search history.

(56) References Cited

U.S. PATENT DOCUMENTS

2010/0311983 A1    12/2010    Kuppuswamy et al.

FOREIGN PATENT DOCUMENTS

| CN | 102399216 A | * | 4/2012 | ........... C07D 417/06 |
| JP | S6028969 A | | 2/1985 | |
| WO | 9426724 A2 | | 11/1994 | |

OTHER PUBLICATIONS

A machine generated English translation of CN 102399216 A (Sun et al.) by Espacenet, 2012. (Year: 2012).*
International Search Report and Written Opinion for Application No. PCT/US2016/051287 dated Nov. 3, 2016.
A machine generated English translation of the JP 6-028969 A (Fujimoto Pharmaceutical Co. Ltd), 1985.

* cited by examiner

*Primary Examiner* — Laura L Stockton
(74) *Attorney, Agent, or Firm* — Mcbee Moore & Vanik IP, LLC

(57) ABSTRACT

The disclosure provides for methods for preparing 2-cyano-imino-1,3-thiazolidine, which is an important building block for the preparation of crop protection active ingredients and pharmaceuticals. To this end, the disclosure provides for more efficient and improved methods of preparing 2-cyano-imino-1,3-thiazolidine.

20 Claims, No Drawings

PROCEDURE FOR THE PREPARATION OF 2-CYANOIMINO-1,3-THIAZOLIDINE

CROSS-REFERENCE TO RELATED APPLICATIONS

This application is a divisional of U.S. application Ser. No. 15/759,574, filed Mar. 13, 2018, which is a national stage application of PCT International Application No. PCT/US2016/051287 filed Sep. 12, 2016, which claims the benefit of U.S. Provisional Application No. 62/218,736 filed Sep. 15, 2015. The contents of which are herein incorporated by reference in their entirety.

FIELD

The disclosure provides for methods for preparing 2-cyanoimino-1,3-thiazolidine ("CIT"), which is a building block for the preparation of crop protection active ingredients and pharmaceuticals. The disclosure further provides for compositions comprising CIT and compounds produced by methods described herein.

BACKGROUND

There is a need to develop new processes for preparing CIT, which is an important building block for the preparation of crop protection active ingredients and pharmaceuticals. To this end, the disclosure provides for more efficient and improved methods of preparing CIT.

The disclosure provides for methods of preparing CIT with advantages over previously known methods of CIT. For example, methods described herein are capable of achieving—production of CIT without the handling of solids until isolation of CIT and/or without purification or isolation of intermediates. Methods described herein are further capable of achieving safer and cheaper production of CIT by employing an aqueous based process that may be completed without the use anhydrous solvents. Surprisingly, as described herein CIT is capable of being produced with the above advantages in equal or better yields as compared to conventional methods of CIT.

SUMMARY

In an aspect, the disclosure provides for methods of preparing CIT, including any of (i), (ii), and/or (iii)
 i. reacting cyanamide with carbon disulfide in the presence of a base to form dimetal N-cyanodithioiminocarbonate;
 ii. reacting dimetal N-cyanodithioiminocarbonate with a methylating agent to form methyl N-cyanodithioiminocarbonate; and/or
 iii. reacting metal methyl N-cyanodithioiminocarbonate with 2-chloroethylammonium hydrochloride to form CIT.

In an aspect, the disclosure further provides for methods of preparing CIT, wherein the method excludes the isolation and/or purification of any intermediates.

The disclosure further provides for methods of preparing CIT, wherein the method excludes the isolation and/or handling of any solid material until the isolation of CIT.

The disclosure further provides methods described herein, wherein the method comprises, consists of, or consists essentially of one or more of the following:
 a. no handling or solid material until isolation of CIT;
 b. intermediates are not isolated during any method steps;
 c. intermediates are not purified, for example, by crystallization, distillation, and/or filtration during methods described herein;
 d. while methods described herein may not include the purification of an intermediate, methods described herein may provide for phase separation in some aspects;
 e. anhydrous solvents are not utilized during method steps; and/or
 f. methods described herein comprise, consist of, or consist essentially of aqueous processing.

In an aspect, methods described herein include one, two, three, four, five, and/or six of (a)-(f). In another aspect, methods described herein include each of (a)-(f).

In another aspect, methods described herein include one, two, three, four, five, and/or six of (a)-(f) and CIT is obtained in equal or greater yield as compared to methods without one, two, three, four, five, and/or six of (a)-(f).

In another aspect, the disclosure provides for methods of preparing CIT wherein methylating agent in step (ii) is selected from the group consisting of a dimethyl sulfate, methyl chloride, and methyl bromide.

In an aspect, the disclosure provides for methods of preparing CIT wherein the solvent in any of steps (i), (ii), and/or (iii) is selected from the group consisting of water, alcohol (for example methanol, and ethanol), ketones (for example, acetone). In another aspect, the solvent includes at least about 50%, at least about 75%, at least about 90%, or at least about 95% water. In yet another aspect, the solvent includes water only. The disclosure further provides for one or more solvent combinations comprising water and excluding methanol.

In another aspect, the disclosure provides for methods of preparing CIT wherein 2-bromoethylammonium hydrochloride or 2-bromoethylammonium hydrobromide is excluded from the preparation of CIT.

The disclosure further provides for methods of preparing CIT, wherein the yield of CIT after steps (1), (2), and (3) is selected from the group consisting of from about 50-about 75%, about 50 to about 70%, about 50-about 60%, about 45 to about 55%, about 50-about 55%, for example, based on cyanamide. The disclosure also provides for methods of preparing CIT, wherein the yield of CIT in step (3) alone is from about 70-to about 99%, from about 75-to about 99%, from about 80-to about 99%, from about 85-to about 99%, from about 90-to about 99%, from about 95-to about 99%, from about 70-to about 95%, from about 80-to about 95%, from about 85-to about 95%, from about 90-to about 98%, at least about 70%, at least about 75%, at least about 80%, at least about 85%, at least about 90%, at least about 95%, at least about 98%, or at least about 99%, for example, based on step (ii) intermediate.

In an aspect, the disclosure provides for methods of preparing CIT, wherein the level of impurities is about 0.1% to about 10%, about 0.1% to about 5%, about 0.1% to about 2%, about 0.1% to about 1%, about 0.2% to about 3%, about 0.2% to about 1%, about 0.1% to about 0.5%, about 0.2% to about 0.4%, less than about 0.2%, less than about 0.3%, less than about 0.5%, less than about 1%, less than about 2%, less than about 5%, or less than about 10%. In an aspect, the level of impurity is measured after the third step and the impurity level includes anything outside of CIT.

In another aspect, the disclosure provides for methods of preparing CIT, wherein the level of organic impurities is about 0.1% to about 5%, about 0.1% to about 2%, about 0.1% to about 1%, about 0.2% to about 3%, about 0.2% to about 1%, about 0.1% to about 0.5%, about 0.2% to about 0.4%, less than about 0.2%, less than about 0.3%, less than about 0.5%, less than about 1%, or less than about 2%. In an aspect, the level of organic impurities is evaluated after the third step of the process. In another aspect, the level of impurity includes anything outside of CIT.

The disclosure further provides for methods of preparing CIT, wherein the yield of CIT after steps (1), (2), and (3) is selected from the group consisting of from about 50-about 75%, about 50 to about 70%, about 50-about 60%, about 45 to about 55%, about 50-about 55%, for example, based on cyanamide and the impurity levels are selected from the group consisting of about 0.1% to about 5%, about 0.1% to about 2%, about 0.1% to about 1%, about 0.2% to about 3%, about 0.2% to about 1%, about 0.1% to about 0.5%, about 0.2% to about 0.4%, less than about 0.2%, less than about 0.3%, less than about 0.5%, less than about 1%, or less than about 2%. In an aspect, the impurities are organic impurities. The disclosure also provides for methods of preparing CIT, wherein the yield of CIT in step (3) alone based on, for example, step (ii) intermediate, is from about 70-to about 99%, from about 75-to about 99%, from about 80-to about 99%, from about 85-to about 99%, from about 90-to about 99%, from about 95-to about 99%, from about 70-to about 95%, from about 80-to about 95%, from about 85-to about 95%, from about 90-to about 98%, at least about 70%, at least about 75%, at least about 80%, at least about 85%, at least about 90%, at least about 95%, at least about 98%, or at least about 99% and with impurity levels selected from the group consisting of about 0.1% to about 5%, about 0.1% to about 2%, about 0.1% to about 1%, about 0.2% to about 3%, about 0.2% to about 1%, about 0.1% to about 0.5%, about 0.2% to about 0.4%, less than about 0.2%, less than about 0.3%, less than about 0.5%, less than about 1%, or less than about 2%. In an aspect, the impurities are organic impurities. In another aspect, the above yields and organic impurities correspond to the yield after the third step.

In an aspect, the yield of steps (1) and (2) described herein is evaluated relative to the yield obtained by the methods described in WO94/26724, which is herein incorporated by reference in its entirety. In an aspect, the yield of step (3) described herein is evaluated relative to the yield obtained by the methods described in JP 60/28969, which is herein incorporated by reference in its entirety.

In another aspect, the disclosure further provides for methods of preparing CIT, wherein the yield of CIT when prepared without the isolation and/or purification of any intermediates is improved relative to the yield of CIT when prepared with the isolation and/or purification of any intermediates by at least about 5%, by at least about 10%, by at least about 20%, by at least about 30%, by at least about 40%, or by at least about 50% or more.

In yet another aspect, the disclosure further provides for methods of preparing CIT, wherein the yield of CIT when prepared (1) without the isolation and/or purification of one or more intermediates and (2) without the isolation and/or handling of any solid material until the isolation of CIT is improved relative to the preparation of CIT (1) with the isolation and/or purification of one or more intermediates and (2) with the isolation and/or handling of solid material until the isolation of CIT and wherein the yields are equal, similar, within about 2%, about 3%, or about 5% of one another, increased by at least about 5%, by at least about 10%, by at least about 20%, by at least about 30%, by at least about 40%, or by at least about 50% or more.

In an aspect, the disclosure provides for methods of preparing CIT, wherein the moles of dimethyl sulfate in step (ii) are selected from the group consisting of about 0.7 to about 1.3, about 0.9 to about 1.2, and about 0.95-1.05 times the moles of cyanamide used in step (i). In yet an aspect, the description provides for methods of preparing CIT wherein the moles of 2-chloroethylammonium hydrochloride in step (iii) are about 0.5 to about 2.0, about 1.0 to about 1.5 times, about 1.1 to about 1.4 times, or about 1.2 to about 1.3 times the moles of cyanamide used in step (i).

In an aspect, the disclosure provides for methods of preparing CIT, wherein the pH in step (iii) is adjusted to about 4 to about 10, about 5 to about 9, or about 5 to about 7 before addition of 2-chloroethylammonium hydrochloride. In another aspect, after initial the pH adjustment, the pH is maintained at about 5 to about 8, about 6 to about 7, about 6 to about 6.8, or about 6 to about 6.5. In yet another aspect, the description provides for methods of preparing CIT, wherein the reaction of step (iii) can be carried out at about 40° C. to about 100° C., about 60° C. to about 80° C., or about 65° C. to about 75° C. and wherein methyl mercaptan is optionally removed from reaction mixture in step (iii).

The disclosure further provides for methods of preparing CIT, wherein after the reaction of step (iii) is complete, it is cooled to about 0° C. to about 50° C., about 0° C. to about 25° C., or about 5° C. to about 15° C. and optionally filtered or purified to isolate CIT.

DETAILED DESCRIPTION

The disclosure provides for a process for preparing CIT. Compounds prepared by methods described herein are also provided for by the disclosure. Compositions comprising CIT prepared by the methods described herein are also provided for by the disclosure.

In an aspect, the disclosure provides for methods of preparing CIT without the isolation and/or purification of intermediates. In another aspect, the disclosure provides for methods of preparing CIT, for example preparing CIT from cyanamide, without the isolation and/or purification of intermediates. In yet another aspect, the yield of CIT when prepared without the isolation and/or purification of intermediates is improved relative to the yield of CIT when prepared with the isolation and/or purification of intermediates. In an aspect, the yield of CIT when prepared without the isolation and/or purification of intermediates is equal, similar, within about 2%, about 3%, or about 5% of one another, or improved relative to the yield of CIT when prepared with the isolation and/or purification of intermediates by at least about 5%, by at least about 10%, by at least about 20%, by at least about 30%, by at least about 40%, or by at least about 50% or more.

The disclosure further provides for methods of preparing CIT without the isolation and/or handling of any solid material. In yet another aspect, the disclosure provides for methods of preparing CIT without the handling of any solid material until the optional isolation and/or purification of CIT. In yet another aspect, the yield of CIT when prepared without the isolation and/or handling of any solid material is equal, within about 2%, 3%, 5%, or 10%, or improved relative to the yield of CIT when prepared with the isolation and/or handling of solid material. In an aspect, the yield of CIT when prepared without the isolation and/or handling of any solid material is equal, within about 2%, 3%, 5%, or 10%, or improved relative to the yield of CIT when prepared with the isolation and/or handling of solid material by at least the same, about 5%, by at least about 10%, by at least about 20%, by at least about 30%, by at least about 40%, or by at least about 50% or more. In an aspect, the yield is evaluated after steps (1)-(3). In another aspect, the yield of steps (1) and (2) described herein is evaluated relative to the yield obtained by the methods described in WO94/26724, which is herein incorporated by reference in its entirety. In an aspect, the yield of step (3) described herein is evaluated relative to the yield obtained by the methods described in JP 60/28969, which is herein incorporated by reference in its entirety.

The disclosure also provides for methods of preparing CIT (1) without the isolation and/or purification of intermediates and (2) without the isolation or handling of solid material until the isolation of CIT. In an aspect, the disclosure provides for methods of preparing CIT from cyanamide (1) without the isolation and/or purification of intermediates and (2) without the isolation or handling of solid material until the isolation of CIT. In another aspect, the disclosure provides for methods of preparing CIT with improved yields, equal yields, or yields within about 2%, 3%, 5%, or 10%, when prepared (1) without the isolation and/or purification of intermediates and/or (2) without the isolation or handling of solid material until the isolation of CIT relative to the preparation of CIT (1) with the isolation and/or purification of intermediates and/or (2) with the isolation or handling of solid material until the isolation of CIT. In yet another aspect, the disclosure provides for methods of preparing CIT with improved yields, equal yields, or yields within about 2%, 3%, 5%, or 10%, when prepared (1) without the isolation and/or purification of intermediates and/or (2) without the isolation or handling of solid material until the isolation of CIT relative to the preparation of CIT (1) with the isolation and/or purification of intermediates and/or (2) with the isolation or handling of solid material until the isolation of CIT wherein the yields are increased by at least about 5%, by at least about 10%, by at least about 20%, by at least about 30%, by at least about 40%, or by at least about 50% or more.

In an aspect, the CIT obtained should be sufficiently pure so that its use in the conversion to Thiacloprid results in in-spec Thiacloprid in good yield without any additional purification steps.

The disclosure further provides methods described herein, wherein the method comprises, consists of, or consists essentially of one or more of the following:
  a. no handling of solid material until isolation of CIT;
  b. intermediates are not isolated during any method steps described herein;
  c. intermediates are not purified, for example, by crystallization, distillation, and/or filtration during methods described herein;
  d. while methods described herein may not include the purification of an intermediate, methods described herein may provide for phase separation in some aspects;
  e. anhydrous solvents are not utilized during method steps;
  f. in an aspect, methods described herein comprise, consist of, or consist essentially of aqueous processing;
  g. NaOH is used during the process; and/or
  h. 2-chloroethylammonium hydrochloride is utilized in the method and in an aspect 2-chloroethylammonium hydrochloride is used instead of 2-bromoethylammonium hydrochloride or hydrobromide.

In an aspect, methods described herein include one, two, three, four, five, six, seven, and/or eight of (a)-(h). In another aspect, methods described herein include each of (a)-(h).

In another aspect, methods described herein include one, two, three, four, five, six, seven and/or eight of (a)-(h) and CIT is obtained in equal or greater yield as compared to methods without one, two, three, four, five, six, seven, and/or eight of (a)-(h).

In an aspect, the disclosure provides for a method of preparing CIT comprising, consisting of, or consisting essentially of each of the following:
  i. reacting cyanamide with carbon disulfide in the presence of a base to form dimetal N-cyanodithioiminocarbonate;
  ii. reacting dimetal N-cyanodithioiminocarbonate with dimethyl sulfate to form metal methyl N-cyanodithioiminocarbonate; and
  iii. reacting metal methyl N-cyanodithioiminocarbonate with 2-chloroethylammonium hydrochloride to form CIT.

In another aspect, the disclosure provides for a method of preparing CIT comprising, consisting of, or consisting essentially of each of the following:
  i. reacting cyanamide with carbon disulfide in the presence of a base to form dimetal N-cyanodithioiminocarbonate;
  ii. reacting dimetal N-cyanodithioiminocarbonate with dimethyl sulfate to form metal methyl N-cyanodithioiminocarbonate; and
  iii. reacting metal methyl N-cyanodithioiminocarbonate with 2-chloroethylammonium hydrochloride to form CIT,
wherein the method excludes the isolation and/or purification of intermediates in any of steps i.-iii.

In another aspect, the disclosure provides for a method of preparing CIT comprising, consisting of, or consisting essentially of each of the following:
  i. reacting cyanamide with carbon disulfide in the presence of a sodium hyhdroxide to form disodium N-cyanodithioiminocarbonate;
  ii. reacting disodium N-cyanodithioiminocarbonate with dimethyl sulfate to form sodium methyl N-cyanodithioiminocarbonate; and
  iii. reacting sodium methyl N-cyanodithioiminocarbonate with 2-chloroethylammonium hydrochloride to form CIT,
wherein the method excludes the isolation or handling of any solid material until the isolation and/or purification of CIT.

In another aspect, the disclosure provides for a method of preparing CIT comprising, consisting of, or consisting essentially each of the following:
  i. reacting cyanamide with carbon disulfide in the presence of a base to form dimetal N-cyanodithioiminocarbonate;
  ii. reacting dimetal N-cyanodithioiminocarbonate with dimethyl sulfate to form metal methyl N-cyanodithioiminocarbonate; and
  iii. reacting metal methyl N-cyanodithioiminocarbonate with 2-chloroethylammonium hydrochloride to form CIT,
wherein the method excludes the isolation or handling of any solid material until the isolation and/or purification of CIT.

In an aspect, the disclosure provides for a method of preparing CIT comprising, consisting of, or consisting essentially of each of the following:
  i. reacting cyanamide with carbon disulfide in the presence of a sodium hydroxide to form disodium N-cyanodithioiminocarbonate;

ii. reacting disodium N-cyanodithioiminocarbonate with dimethyl sulfate to form sodium methyl N-cyanodithioiminocarbonate; and
iii. reacting sodium methyl N-cyanodithioiminocarbonate with 2-chloroethylammonium hydrochloride to form CIT.

In another aspect, the disclosure provides for a method of preparing CIT comprising, consisting of, or consisting essentially of each of the following:
i. reacting cyanamide with carbon disulfide in the presence of a sodium hydroxide to form di sodium N-cyanodithioiminocarbonate;
ii. reacting disodium N-cyanodithioiminocarbonate with dimethyl sulfate to form sodium methyl N-cyanodithioiminocarbonate; and
iii. reacting sodium methyl N-cyanodithioiminocarbonate with 2-chloroethylammonium hydrochloride to form CIT,
wherein the method excludes the isolation and/or purification of intermediates in any of steps i.-iii.

In another aspect, methods described herein display advantages over standard methodology of producing CIT from cyanamide. In an aspect, the standard methodology involves preparation of dimethyl N-cyanodithioiminocarbonate and reacting dimethyl N-cyanodithioiminocarbonate with cysteamine hydrochloride. This route has been described in, for example, WO 2009/033583A1 and WO 2009/113098A2, each if which are herein incorporated by reference in their entirety. Some of the advantages of the methodology described herein over the standard methodology described in, for example, WO 2009/033583A1 and WO 2009/113098A2, include the following:
i. The standard route requires two equivalents of dimethyl sulfate while in certain aspects the methodology described herein includes only one equivalent.
ii. The standard route generates two equivalents of noxious methyl mercaptan in certain aspects the methodology described herein generates one equivalent.
iii. The standard route uses cysteamine hydrochloride which is more difficult to prepare and is more expensive than 2-choroethylammonium hydrochloride.

Preparation of Dimetal N-cyanodithioiminocarbonate (Step 1)

In an aspect, the disclosure provides for a method of reacting cyanamide with carbon disulfide in the presence of a base, for example, KOH or NaOH, to form dimetal N-cyanodithioiminocarbonate as shown in the scheme below (Scheme I):

Scheme I

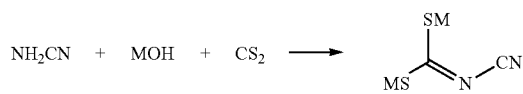

wherein "M" is a metal, for example, a metal from groups 1 and 2 of the periodic table.

In an aspect, the stoichiometry of cyanamide to base to carbon disulfide can be varied in an amount sufficient to prepare dimetal N-cyanodithioiminocarbonate. In another aspect, the molar ratio of cyanamide to base to carbon disulfide is 1.0:2.0:1.0. The disclosure also provides for up to 10%, 20%, 30%, or 40% variation in the mole ratios.

In an aspect, water alone is used as a solvent. In another aspect, one or more of the following may be used, for example, water, alcohol, such as methanol or ethanol, ketones, such as acetone, or combinations thereof. The disclosure also provides for a solvent of alcohol alone or ketones alone. In another aspect, the solvent includes at least about 50%, at least about 75%, at least about 90%, at least about 95% water.

In yet another aspect, methanol is excluded as a solvent. In yet another aspect, the solvent includes at least about 50%, at least about 75%, at least about 90%, at least about 95% water and methanol is excluded as the solvent.

In addition to water as a solvent, the solvent may include one or more of the following with or without water, organic solvents, halohydrocarbons, chlorohydrocarbons, tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols such as methanol, ethanol, isopropanol, butanol; ethers such as ethyl propyl ether, methyl tert-butyl ether, methyl n-butyl ether, anisole, phenetol, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, dioxane, dichlorodiethyl ether, and polyethers of ethylene oxide and/or of propylene oxide; amines such as trimethyl-, triethyl-, tripropyl- and tributylamine, N-methylmorpholine, pyridine, alkylated pyridines and tetramethylenediamine; nitrohydrocarbons such as nitromethane, nitroethane, nitropropane, nitrobenzene, chloronitrobenzene, o-nitrotoluene; nitriles such as acetonitrile, methyl nitrile, propionitrile, butyronitrile, isobutyronitrile, benzonitrile, phenyl nitrile, m-chlorobenzonitrile, and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methyl ethyl, ethyl propyl, ethyl isobutyl and pentamethylene sulphone; aliphatic, cycloaliphatic or aromatic hydrocarbons such as pentane, hexane, heptane, octane, nonane, cyclohexane, methylcyclohexane, petroleum ether, ligroin, octane, benzene, toluene, chlorobenzene, bromobenzene, nitrobenzene, xylene; esters such as methyl, ethyl, butyl and isobutyl acetate, and dimethyl, dibutyl and ethylene carbonate; amides such as hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; ketones such as acetone, acetophenone, methyl ethyl ketone, methyl butyl ketone.

In an aspect, the disclosure provides for a cyanamide concentration of from about 1% to about 20%, about 2 to about 15%, about 3 to about 10%, about 5% to about 10%, or about 6% to 9% by weight in the reaction mixture.

The disclosure also provides for the addition of a base to a cyanamide solution at a temperature range from about −10° C. to about 40° C., from about −10° C. to about 20° C., from about 0° C. to about 20° C., from about 0° C. to about 15° C., or from about 0° C. to about 10° C., less than about 15° C., or less than about 10° C. In an aspect, the disclosure provides for the addition of carbon disulfide to a cyanamide salt solution at a temperature range from about −10° C. to about 40° C., from about −10° C. to about 20° C., from about 0° C. to about 20° C., or from about 0° C. to about 15° C. In yet another aspect, the disclosure provides for a postcook temperature of from about 0° C. to about 40° C., from about 5° C. to about 35° C., from about 10° C. to about 30° C., or from about 15° C. to about 25° C.

In an aspect, metal hydroxides with metals from groups 1 and 2 of the periodic table can be used as a base. In an aspect, the base may include sodium, potassium, or combinations thereof.

In an aspect, the base is added to a cyanamide solution first and then carbon disulfide is added. However, the disclosure further provides for an embodiment where any addition order of the reactants is possible or two or more reactants can be added simultaneously.

In an aspect, a base can be added to cyanamide at a rate such that the temperature remains below about 40° C., below about 30° C., below about 20° C., below about 15° C. during the addition. In an aspect, carbon disulfide can be added all at once or over several hours, for example, up to about 6 hours, about 12 hours, or about 24 hours or more.

In an aspect, the reaction is completed in about 2 to about 24 hours, about 5 to 20 hours, about 10 to 20 hours, or an additional time frame depending on concentration of reactants and temperature.

In an aspect, the reaction can be carried out with or without the use of a catalyst, such as a phase transfer catalysts. Use of phase transfer catalyst can accelerate the reaction with carbon disulfide in certain embodiments. In an aspect, phase transfer catalysts can be chosen from a variety of tetraalkylammonium or tetraalkylphosphonium based catalysts. For example, the disclosure provides for a phase transfer catalyst selected from the group consisting of either methyltrioctylammonium chloride or methyltributylammonium chloride. In an aspect, if a catalyst is employed, the concentration may be from about 0.01 to about 1.0, from about 0.05 to about 0.8, from about 0.1 to about 0.5 weight percent of reaction mixture.

Preparation of Metal Methyl
N-cyanodithioiminocarbonate (Step 2)

In an aspect, the disclosure provides for a method of reacting disodium N-cyanodithioiminocarbonate with methylating agent, for example, dimethyl sulfate, to form sodium methyl N-cyanodithioiminocarbonate. In another aspect, the disclosure provides for a method of reacting disodium N-cyanodithioiminocarbonate as prepared in accordance with the section labeled "preparation of dimetal N-cyanodithioiminocarbonate" above with dimethyl sulfate to form sodium methyl N-cyanodithioiminocarbonate as shown in the equation below (Scheme II):

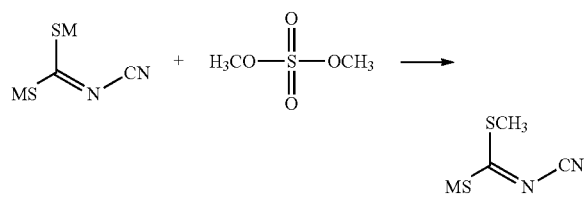

Scheme II wherein "M" is a metal, for example, a metal from groups 1 and 2 of the periodic table.

In an aspect, the methylating agent described herein is selected from the group consisting of dimethyl sulfate, methyl chloride, and/or methyl bromide.

In an aspect, the moles of dimethyl sulfate used in this step are about 0.7 to about 1.3, about 0.9 to about 1.2, or about 0.95-1.05 times the moles of cyanamide used in the section entitled the section labeled "preparation of dimetal cyanodithioiminocarbonate" (step 1) above.

In another aspect, the disclosure provides for a solvent comprising a mixture of water and toluene, water in combination with other aromatic, cyclic or acyclic (substituted and unsubstituted) hydrocarbons such as xylenes, hexanes, alcohols such as methanol, ethanol, ketones such as acetone, methylisobutyl ketone or combinations thereof. Esters and ethers typically used as industrial solvents can also be used in some aspects.

In an aspect, the concentration of the reactant disodium N-cyanodithioiminocarbonate in the reaction mixture is determined by the reaction conditions used in the section entitled the section labeled "preparation of dimetal cyanodithioiminocarbonate" (step 1) above. In an aspect, step 2 can be carried out with or without adding any additional water or other solvents. In another aspect, a small amount (about 5 to about 10% of the weight of the reaction mixture) of toluene is added prior to the addition of dimethyl sulfate.

In another aspect, methylation can be carried out without adding an acid (lowering the pH). However, in certain aspects the performance of the reaction may be improved if the pH is lowered first by addition of acid. Any commonly used acids such as hydrochloric, sulfuric, nitric, acetic, phosphoric, methanesulfonic, formic etc. can be used. In an aspect, 36% aqueous hydrochloric acid is used.

In an aspect, methylation can be carried out in a pH range of from about 3 to about 13, about 5 to about 10, or about 8 to about 10. In an aspect, the pH is lowered to about 8 to about 10 by addition of acid prior to the addition dimethyl sulfate to improve the yield and selectivity of this methylation step.

Addition of dimethyl sulfate to dimetal N-cyanodithioiminocarbonate solution can be carried out at about −10° C. to about 50° C., about 0° C. to about 40° C., about −0° C. to about 20° C., or about 0° C. to about 15° C.

To minimize the formation of the main byproduct (dimethyl N-cyanodithioiminocarbonate), dimethyl sulfate is added to the solution of dimetal N-cyanodithioiminocarbonate.

In an aspect, addition of dimethyl sulfate to dimetal N-cyanodithioiminocarbonate solution can be carried out at such a rate that temperature remains below about 50° C., about 40° C., about 30° C., or about 20° C. during the addition. In another aspect, addition of dimethyl sulfate to dimetal N-cyanodithioiminocarbonate solution carried out at such a rate that the temperature of the reaction mixture remains from about 0 to about 20° C. or about 5° C. to about 15° C. In an aspect, the reaction takes about 1 to about 4 hours but can be carried out over a period of about 0.5 hours to about 24 hours in another aspect.

In an aspect, the methylation reaction takes from about 5 to about 30, from about 10 minutes to 60 minutes, or about 10 minutes to about 2 hours after the dimethyl sulfate addition is complete to ensure complete reaction.

After the methylation is complete, methods described herein can include a pH adjustment step wherein the pH is lowered to arrange of from about 2 to about 10, about 3 to about 9, or about 6 to about 8. Any commonly used acids such as hydrochloric, sulfuric, nitric, acetic, phosphoric, methanesulfonic, formic etc. can be used. In an aspect, 36% aqueous hydrochloric acid is used.

Preparation of 2-cyanoimino-1,3-thiazolidine (CIT) (Step 3)

Metal methyl N-cyanodithioiminocarbonate formed in step 2 above can be reacted with 2-chloroethylammonium hydrochloride to form CIT as shown in the equation below (Scheme III):

Scheme III

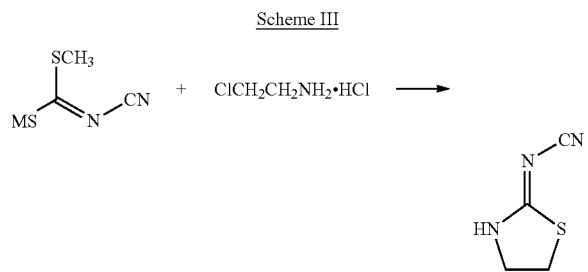

wherein "M" is a metal, for example, a metal from groups 1 and 2 of the periodic table.

In an aspect, the moles of 2-chloroethylammonium hydrochloride used in this step are 0.5 to about 2.0 about 1.0 to about 1.5 times, 1.1 to about 1.4 times, or 1.2 to about 1.3 times the moles of cyanamide used in step 1. In addition to the hydrochloride salt, other suitable salts such as hydrobromide, hydrogen sulfate, phosphate etc. of 2-chloroethylamine can also be used.

In an aspect, 2-chloroethylammonium hydrochloride is added to the reaction mixture as about a 70 weight % aqueous solution. In another aspect, 2-chloroethylammonium hydrochloride can also be added either as a solid or an aqueous solution of concentration from 10 weight % up to the saturation point.

In an aspect, water alone is used as a solvent. In another aspect, aromatic, cyclic or acyclic (substituted and unsubstituted) hydrocarbons such as xylenes, hexanes, alcohols such as methanol, ethanol, ketones such as acetone, methylisobutyl ketone can also be used. Esters and ethers typically used as industrial solvents can also be used either by themselves or in combination with water.

In an aspect, the concentration of the reactants in the reaction mixture is determined by the reaction conditions used in step 1 and 2. Step 3 can be carried out with or without adding any additional water or other solvents.

In an aspect, the pH can be adjusted to about 4 to about 10 or about 5 to about 7 before addition of 2-chloroethylammonium hydrochloride.

In an aspect, any commonly used acids such as hydrochloric, sulfuric, nitric, 36% aqueous hydrochloric acid, acetic, phosphoric, methanesulfonic, formic etc. can be used for the pH adjustment.

2-chloroethylammonium hydrochloride can be added either all upfront or over about several hours, for example, about 2 to about 12 hours, about 1 to about 5 hours, about 1 to about 3 hours, or about 2 to about 5 hours to the solution of metal methyl N-cyanodithioiminocarbonate while maintaining the desired pH and temperature. Reverse mode of addition in which the solution of sodium methyl N-cyanodithioiminocarbonate is added to 2-chloroethylammonium hydrochloride is also possible as long as desired pH range and temperature is maintained. In another aspect, simultaneous addition can be pursued. In another aspect, an about 70% aqueous solution of 2-chloroethylammonium hydrochloride is added over to about 30 minutes to about 24 hours, about 1 to about 12 hours, or about 2 to about 4 hours to the solution of metal methyl N-cyanodithioiminocarbonate while maintaining the desired pH and temperature ranges.

In an aspect, the disclosure provides for coupling of a monomethyl compound metal salt with 2-chloroethylammonium hydrochloride. In an aspect, methods provided herein utilize 2-chloroethylammonium hydrochloride while 2-bromoethylammonium hydrobromide or 2-bromoethylammonium hydrochloride is excluded. In another aspect, methods described herein utilizing 2-chloroethylammonium hydrochloride provide for a similar or a higher end product yield, for example, about 5% or more, about 10% or more, about 20% or more, about 30% or more, or about 50% or more as compared to when a 2-bromoethylammonium hydrochloride or 2-bromoethylammonium hydrobromide is used in the same reaction. In an aspect, the 2-chloroethylammonium hydrochloride gives a very good yield in spite of chloro compounds generally being less reactive than corresponding bromo compounds. In yet another aspect, methods herein exclude a potassium salt.

In an aspect, the reaction can be carried out at about 40° C. to about 100° C., about 60° C. to about 80° C., or about 65° C. to about 75° C. In another aspect, these temperatures ranges are maintained throughout the reaction.

In another aspect, the pH is maintained from about 4 to about 10, about 5 to about 9, about 6 to about 8, or about 5.5 to about 7.5 by simultaneous addition of base. In an aspect, commonly used bases such as hydroxides, carbonates, bicarbonates, phosphates, alkoxides from groups 1 and 2 of the periodic table can be used either as a solid or as an aqueous solution. In an aspect, sodium or potassium hydroxide can be used.

In an aspect, the reaction is continued until it is at least about 80%, at least about 85%, at least about 90%, at least about 95%, or at least about 99% complete as determined by HPLC analysis of the reaction mixture. If needed, the temperature of the reaction mixture can be raised by a few degrees to drive the reaction towards completion.

In an aspect, methyl mercaptan is removed from reaction mixture. Methyl mercaptan is formed as a byproduct during this step. Since at the operating pH it is present as methyl mercaptan (not as a salt) and since its boiling point is only 6° C. and is not much soluble in an aqueous reaction mixture, most of it escapes from the reaction flask as it is formed. To minimize odor issues, it can be led via tubing into a flask containing sodium hypochlorite to oxidize it to less odorous products or into a solution of aqueous base to convert it into methyl mercaptan salts which are less odorous. Alternatively, the methyl mercaptan can be removed from the reaction mixture by application of a slight vacuum during the reaction. In another aspect, methyl mercaptan is removed at the end of the reaction.

After the reaction is complete, it is cooled to about 0° C. to about 50° C., about 0° C. to about 25° C., or about 5° C. to about 15° C. and filtered to isolate the CIT. Optionally, prior to or after cooling, it can be mixed with solvents such as alcohols (such as methanol, ethanol, butanol) or nitriles (such as acetonitrile) or hydrocarbons (such as toluene, xylenes, hexane.) or ketones (such as acetone, methylisobutyl ketone) or esters (such as ethyl acetate) or ethers (such as methyl tert-butyl ether) which can in some cases lead to purer product. The filtered product can then be washed with water or water in combination with one or more of the solvents mentioned above.

In an aspect, the disclosure provides for a method comprising, consisting of, or consisting essentially of steps 1 to 3. In an aspect, the disclosure provides for a method comprising, consisting of, or consisting essentially of steps 2 to 3. In yet another aspect, the disclosure provides for a method comprising, consisting of, or consisting essentially of step 3.

In another aspect, no intermediates are isolated or purified in any of steps 1 to 3. In yet another aspect, no intermediates are isolated or purified in any of steps 1, 2, or 3, individually or in combination. In an aspect, no solids (prior to isolation of CIT) are isolated or handled in any of steps 1, 2, or 3, individually or in combination. In yet another aspect, (1) no intermediates are isolated or purified in any of steps 1, 2, or 3 individually or in combination and (2) no solids (prior to isolation of CIT) are isolated or handled in any of steps 1, 2, or 3, individually or in combination.

In an aspect, CIT described by methods described herein are used to produce Thiacloprid.

EXAMPLES

Example 1

Example 1 describes a method of preparing CIT from cyanamide.

Preparation of Disodium N-cyanodithioiminocarbonate (Step 1)

Scheme I

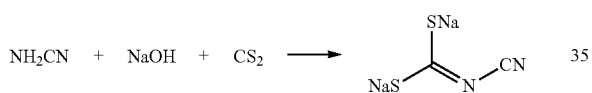

In a 250 ml round bottom flask equipped with a magnetic stir bar, addition funnel, and a water condenser was charged, cyanamide (21.0 g, 50% aq. solution, 0.25 moles) and water (95 g). The solution was chilled in an ice-water bath until the temperature was <5° C. Sodium hydroxide (40.0 g, 50% aq. solution, 0.50 moles) was added to this solution at such a rate that the pot temperature remained below 10° C. throughout the addition (about 45 minutes). The solution was stirred in an ice-water bath for approximately 15 minutes and 0.20 g of phase transfer catalyst methyltributylammonium chloride (MTBCl) was added to the flask. A cold-finger filled with ice was then put on top of the water condenser to minimize escape of carbon disulfide from the flask. 19 grams of carbon disulfide was added to the flask in one portion and the ice-water bath was removed. The reaction mixture was then allowed to come to room temperature and stirred overnight at room temperature. A semi-clear solution was obtained. About 174 g of reaction mixture was obtained.

Preparation of Sodium Methyl N-cyanodithioiminocarbonate (Step 2)

Scheme II

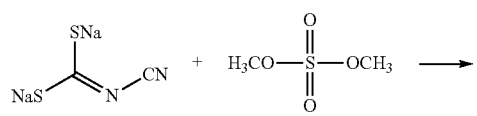

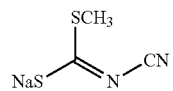

The reaction mixture from step 1 above was treated with hydrochloric acid (36%) added dropwise to a pH of about 9 to about 9.5. It was then mixed with toluene (20 g) and chilled in an ice-water bath to <5° C. Dimethyl sulfate (31.9 g, 0.253 moles) was then added at such a rate that the reaction temperature remained <15° C. during the addition. After the addition was complete, it was allowed to stir in ice-water bath for 30 minutes and the reaction mixture was then treated dropwise with hydrochloric acid (36%) till pH dropped from about 9.5 to about 7.0. Stirring was then stopped to allow the phases to separate. The organic phase was discarded and the aqueous phase containing the sodium methyl N-cyanodithioiminocarbonate was collected for the next step. About 203 g of the aqueous phase was collected.

Preparation of 2-cyanoimino-1,3-thiazolidine (CIT) (Step 3)

Scheme III

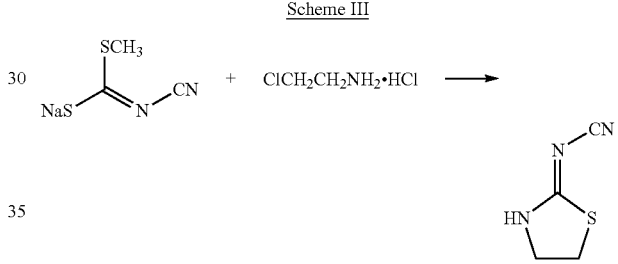

The aqueous phase from step 2 above was taken in a 500 ml round bottom flask equipped with a water condenser, magnetic stir bar, pH probe and an addition funnel. Methyl mercaptan was removed via a hypo-scrubber. The solution was heated to 70° C. and the 2-chloroethylammonium hydrochloride (53.6 g, 70% solution in water, 0.32 moles) was added via addition funnel over about 4 hours maintaining pH about 6.0 to about 6.8 preferably about 6.4 by simultaneous addition of sodium hydroxide (50% aqueous). After the addition was complete, the reaction mixture was stirred at 70° C. until the reaction was >98% complete, as determined by HPLC. Typically, it took about 2 hours of postcook to reach this stage. At the end of the postcook, the reaction mixture was a thin, white slurry and the pH fell fairly slowly. At this point, the heating was stopped and a slight vacuum was applied at the top of the condenser to remove methyl mercaptan. As the reaction mixture cooled in the oil bath, the vacuum was slowly increased (in such a way to avoid foaming and boil-over) reaching full house vacuum (about 200 mm) by the time the reaction mixture cooled to 40° C. The vacuum was then discontinued, toluene (20 g) was added, and the reaction mixture was allowed to come to room temperature by removing the oil bath and then cooled to about 5° C. in an ice-water bath. After stirring for about 1 hour at this temperature, the reaction mixture was filtered under house vacuum (200 mm) on a Buchner funnel. The cake was allowed to dry on the funnel under house vacuum at room temperature till constant weight was obtained. CIT was obtained in 79.9 weight % purity (organic impurities were about 1.9%, rest of the impurities were inorganic salts) and in 61% yield of 100% CIT based on cyanamide and about 8% of the yield of CIT was present in the mother liquor of the filtration. When this dried CIT was stirred in a flask at room temperature in 3 times the weight of water for 1 hour, filtered, and dried, the purity went up to 91.5% and the organic impurities dropped to about 1.5%.

Example 2

Example 2 describes a method of preparing disodium N-cyanodithioiminocarbonate utilizing a reduced amount of water.

Cyanamide (21.0 g, 50% aq. solution, 0.25 moles) and water (30.0 g) was added to a 250 ml round bottom flask equipped with a magnetic stir bar, addition funnel, and a charged water condenser. The solution was chilled in an ice-water bath until the temperature was <5° C. A mixture of sodium hydroxide (40.0 g, 50% aq. solution, 0.50 moles) and water (10.0 g) at such a rate that the pot temperature remained below 10° C. throughout the addition (took about 55 minutes) was added to this solution. This mixture was stirred in an ice-water bath for 15 minutes and 0.23 g of phase transfer catalyst methyltrioctylammonium chloride (Aliquat 336) was added to the flask. Next, a cold-finger filled with ice was put on top of the water condenser to minimize escape of carbon disulfide from the flask. Carbon disulfide (19.0 g) was added to the flask in one portion and the ice-water bath was removed. Next, the reaction mixture adjusted to room temperature and was stirred. A small known weight of the reaction mixture was mixed with a known weight of an internal standard (N,N-dimethylpropionamide) after 7 hours of stirring and analyzed on LC. A similar analysis was performed for the same reaction after stirring overnight (16 hours) at room temperature. Comparison of the two analyses indicates that a reduction in water used (as compared to that in step 1 of Example 1), and also due to the use of Aliquat 336 (instead of MTBCl) as catalyst, the reaction was complete in 7 hours.

Example 3

Example 3 describes a method of preparation of disodium N-cyanodithioiminocarbonate.

Cyanamide (42.0 g, 50% aq. solution, 0.50 moles) and water (40.0 g) was added to a 500 ml round bottom flask equipped with a magnetic stir bar, addition funnel, and charged water condenser. The solution was chilled in an ice-water bath until the temperature was <5° C. A mixture of sodium hydroxide (80.0 g, 50% aq. solution, 0.50 moles) and water (40.0 g) to the solution at such a rate that the pot temperature remained below 10° C. throughout the addition (took about 70 minutes). The mixture was stirred in an ice-water bath for 15 minutes and 0.46 g of phase transfer catalyst methyltrioctylammonium chloride (Aliquat 336) was added to the flask. Next, a cold-finger filled with ice was put on top of the water condenser to minimize escape of carbon disulfide from the flask. Carbon disulfide (38.4 g) was added to the flask in one portion and the ice-water bath was removed. The reaction mixture was calibrated to room temperature and stirred overnight (16 hours). The reaction mixture was subjected to slight vacuum (about 200 mm) for 15 minutes to remove excess carbon disulfide. This solution of disodium N-cyanodithioiminocarbonate (240.9 g) was used in portions for studying different modes of additions of 2-chloroethylammonium hydrochloride described below.

This solution contained approximately 0.425 moles of disodium N-cyanodithioiminocarbonate.

Example 4

Example 4 describes preparation of CIT using upfront addition of 2-chloroethylammonium hydrochloride.

A solution of disodium N-cyanodithioiminocarbonate (45.0 g, prepared in example 3 above, containing approximately 0.079 moles), water (20.5 g) and toluene (7.5 g) was added to a 250 ml round bottom flask equipped with a magnetic stir bar, addition funnel, and a charged water condenser. The pH of the solution was adjusted to between 9.0 and 9.5 with the drop wise addition of 36% aqueous HCl and chilled in an ice-water bath to less than 5° C. Dimethyl sulfate (12.2 g, 0.097 moles) was added to this solution at such a rate that the temperature of the reaction mixture remained below 10° C. at all times during the addition. The reaction mixture was stirred for 15 minutes and treated with the drop wise addition of 36% aqueous HCl until pH 7.2 was achieved. The aqueous phase (76.4 g, which contained approximately 0.071 moles of the sodium methyl N-cyanodithioiminocarbonate) was collected for the next step and the organic phase was discarded. 2-chloroethylammonium hydrochloride (20.0 g, 70% aqueous solution, 0.12 moles) was added to this phase in one portion and heated to 70° C. The pH of the reaction mixture was maintained between 6.3 and 6.8 by concomitant addition of 50% aq NaOH solution. Methyl mercaptan formed during the reaction was led into a trap containing sodium hypochlorite aqueous solution. The reaction mixture was stirred at 70° C. for 2 h and at 75° C. for 1 hour. By this time, the pH was falling very slowly and analysis of the reaction mixture showed that unreacted sodium methyl N-cyanodithioiminocarbonate was less than 1%. Next, the heating was stopped and a slight vacuum was applied as the reaction cooled to room temperature to remove most of the remaining methyl mercaptan from the reaction mixture. The solution was allowed to come to room temperature and filtered. The solids on the funnel were washed once with 10 g water and dried to a constant weight under house vacuum on the funnel at room temperature. Weight of the dried CIT product was 6.9 g and as purity was 96.5%. The organic impurities as seen on LC were 0.2% while the rest were inorganic salts, for example, sodium methyl sulfate and sodium chloride. The isolated yield of CIT based on cyanamide was 56.1%.

Example 5

Example 5 describes a preparation of CIT using a 4 hour addition of 2-chloroethylammonium hydrochloride.

The procedure and the charges used in this example were same as in example 4 above except that the 2-choroethylammonium hydrochloride 70% aqueous solution was added over a 4 hour period (instead of all up front). The weight of the dried CIT product was 6.6 g and the purity was 98.7%. The organic impurities as seen on LC were 0.2% while the rest were inorganic salts, for example, sodium methyl sulfate and sodium chloride. The isolated yield of CIT based on cyanamide was 54.9%.

Example 6

Example 6 describes the preparation of CIT using a simultaneous addition of sodium methyl N-cyanodithioiminocarbonate and 2-chloroethylammonium hydrochloride.

At first, water (5.0 g) and aqueous phase from the methylation (5.0 g, which containing approximately 0.0046 moles of the sodium methyl N-cyanodithioiminocarbonate, prepared as in Example 4 above) were taken in a 250 ml round bottom flask. The remaining aqueous phase from the methylation (71.4 g, containing approximately 0.066 moles of the sodium methyl N-cyanodithioiminocarbonate) and 70% aqueous solution of 2-chloroethylammonium hydrochloride (20.0 g, 70% aqueous solution, 0.12 moles) were mixed in an addition funnel and this mixture was added to the flask over 4 hours at 70-75° C. maintaining the pH of the reaction mixture between 6.3 and 6.8 with concomitant addition of 50% aqueous NaOH. The rest of the procedure was the same as in Example 4 above. Here, the weight of the dried CIT product was 6.9 g with a purity of 97.8%. The organic impurities as seen on LC were 0.9% while the rest were inorganic salts, for example, sodium methyl sulfate and sodium chloride. The isolated yield of CIT based on cyanamide was 56.9%.

Example 7

Example 7 describes a procedure for the evaluation of CIT.

In a single neck 100 ml round bottom flask, 2.0 g of CIT (unwashed, 79.9% A.I., 12.6 mmoles), water (14.0 g), CCMP solution in toluene (6.6 g, 35% w/w, 14.2 mmoles), Aliquat 336 (2 drops, ~0.04 g), sodium carbonate (3.4 g, 32.1 mmoles), were added and the mixture was stirred at about 75° C. for 2-3 hours and sampled on LC to confirm that the reaction was >99.5% complete with respect to CIT. The reaction mixture was then diluted with 1.5 g n-butanol, the heating was turned off and allowed to cool to room temperature in oil bath with stirring. It was then filtered and washed on the funnel (without mixing) with a mixture of 10 g water+5 g toluene and analyzed on LC. The organic impurities (as seen at 240 nm wavelength assuming a default 1.00 response factor for all compounds) were about 0.5% and the absolute purity was about 89%. The yield of thiacloprid based on CIT was estimated to be about 88% and there was about 8.5% loss of yield to the mother liquor and about 0.5% loss of yield to the wash.

The invention claimed is:
1. A method of preparing thiacloprid comprising:
   i) in a solvent, reacting cyanamide with carbon disulfide in the presence of a base to form dimetal N-cyanodithioiminocarbonate;
   ii) in a solvent, reacting dimetal N-cyanodithioiminocarbonate with a methylating agent to form metal methyl N-cyanodithioiminocarbonate;
   iii) in a solvent, reacting metal methyl N-cyanodithioiminocarbonate with 2-chloroethylammonium hydrochloride to form 2-cyanoimino-1,3-thiazolidine; and
   iv) reacting 2-cyanoimino-1,3-thiazolidine with cCMP in toluene; water; Aliquat 336; and sodium carbonate to produce Thiacloprid;
   wherein the method excludes the isolation and/or purification of one or more intermediates from one or more of steps (i), (ii), or (iii).
2. The method of claim 1, wherein said method excludes the isolation and/or handling of any solid material until the isolation and/or purification of 2-cyanoimino-1,3-thiazolidine from one or more of steps (i), (ii), or (iii).
3. The method of claim 1, wherein the methylating agent in step (ii) is selected from the group consisting of a dimethyl sulfate, methyl chloride, and methyl bromide.
4. The method of claim 1, wherein the solvent in any of steps (i), (ii), or (iii) is selected from the group consisting of water, alcohols, ketones, methanol, ethanol, acetone, and methyl isobutyl ketone.
5. The method of claim 4, wherein the solvent comprises at least about 95% water.
6. The method of claim 1, wherein the yield based on cyanamide of 2-cyanoimino-1,3-thiazolidine after steps (i), (ii), and (iii) is about 50 to about 60%.
7. The method of claim 1, wherein the use of a 2-bromoethylammonium hydrochloride or 2-bromoethylammonium hydrobromide is excluded therefrom.
8. The method of claim 1, wherein the methylating agent is dimethyl sulfate.
9. The method of claim 8, wherein the moles of dimethyl sulfate in step (ii) are selected from about 0.9 to about 1.2 times the moles of cyanamide used in step (i).
10. The method of claim 1, wherein the moles of 2-chloroethylammonium hydrochloride in step (iii) are about 1.0 to about 1.5 times the moles of cyanamide used in step (i).
11. The method of claim 1, wherein water alone is used as a solvent in step (i).
12. The method of claim 1, wherein water alone is used as a solvent in step (iii).
13. The method of claim 1, wherein the pH in step (iii) is adjusted to about 5 to about 9 before addition of 2-chloroethylammonium hydrochloride.
14. The method of claim 1, wherein the 2-chloroethylammonium hydrochloride is added to the reaction mixture in an amount of up to about 80 weight % or as a solid in step (iii).
15. The method of claim 1, wherein methyl mercaptan is removed from reaction mixture in step (iii).
16. The method of claim 1, wherein after the reaction of step (iii) is complete, the 2-cyanoimino-1,3-thiazolidine is cooled to about 0° C. to about 25° C.
17. A method of preparing thiacloprid comprising:
   i) reacting cyanamide with carbon disulfide in the presence of sodium hydroxide and methyltrioctylammonium chloride to form disodium N-cyanodithioiminocarbonate;
   ii) reacting disodium N-cyanodithioiminocarbonate with dimethyl sulfate to form sodium methyl N-cyanodithioiminocarbonate;
   iii) reacting sodium methyl N-cyanodithioiminocarbonate with 2-chloroethylammonium hydrochloride to form 2-cyanoimino-1,3-thiazolidine; and
   iv) reacting 2-cyanoimino-1,3-thiazolidine with cCMP in toluene; water; Aliquat 336; and sodium carbonate to produce Thiacloprid;
   wherein the method excludes the isolation and/or purification of one or more intermediates from one or more of steps (i), (ii), or (iii).
18. The method of claim 17, wherein said method excludes the isolation and/or handling of any solid material until the isolation and/or purification of 2-cyanoimino-1,3-thiazolidine from one or more of steps (i), (ii), or (iii).
19. The method of claim 17, wherein methyl mercaptan is removed from the reaction mixture in step (iii).
20. The method of claim 4, wherein the solvent comprises at least about 50% water.

* * * * *